US011896560B2

(12) United States Patent
Callahan et al.

(10) Patent No.: US 11,896,560 B2
(45) Date of Patent: Feb. 13, 2024

(54) CANNABINOID DOSING REGIME FOR DERMATITIS AND INFLAMMATORY SKIN CONDITIONS

(71) Applicant: Botanix Pharmaceuticals LTD, North Perth (AU)

(72) Inventors: Matthew Callahan, Philadelphia, PA (US); Michael Thurn, Kangaroobie (AU)

(73) Assignee: Botanix Pharmaceuticals Ltd., Plymouth Meeting, PA (US)

( * ) Notice: Subject to any disclaimer, the term of this patent is extended or adjusted under 35 U.S.C. 154(b) by 363 days.

(21) Appl. No.: 16/964,791

(22) PCT Filed: Jan. 24, 2019

(86) PCT No.: PCT/AU2019/050051
§ 371 (c)(1),
(2) Date: Jul. 24, 2020

(87) PCT Pub. No.: WO2019/144190
PCT Pub. Date: Aug. 1, 2019

(65) Prior Publication Data
US 2021/0052511 A1 Feb. 25, 2021

Related U.S. Application Data

(60) Provisional application No. 62/621,225, filed on Jan. 24, 2018, provisional application No. 62/736,052, filed on Sep. 25, 2018.

(30) Foreign Application Priority Data

Jan. 24, 2018 (AU) ................................ 2018900226
Sep. 25, 2018 (AU) ................................ 2018903600

(51) Int. Cl.
*A61K 31/05* (2006.01)
*A61P 17/00* (2006.01)
*A61K 9/00* (2006.01)
*A61K 9/06* (2006.01)
*A61K 47/24* (2006.01)

(52) U.S. Cl.
CPC ............ *A61K 31/05* (2013.01); *A61K 9/0014* (2013.01); *A61K 9/06* (2013.01); *A61K 47/24* (2013.01); *A61P 17/00* (2018.01)

(58) Field of Classification Search
CPC ..................................................... A61K 31/05
See application file for complete search history.

(56) References Cited

U.S. PATENT DOCUMENTS

| 2010/0273895 | A1* | 10/2010 | Stinchcomb | ............ | A61P 17/14 |
| | | | | | 514/733 |
| 2016/0374958 | A1 | 12/2016 | Anastassov et al. | | |
| 2017/0112855 | A1* | 4/2017 | Modi | .................. | A61K 31/573 |
| 2021/0401768 | A1 | 12/2021 | Cooper et al. | | |

FOREIGN PATENT DOCUMENTS

| CA | 2971197 | | 12/2018 |
| EP | 24441081 | * | 4/2015 |
| WO | WO 2002/065997 | | 8/2002 |
| WO | WO 2003/007901 | | 1/2003 |
| WO | WO 2008/024408 | | 2/2008 |
| WO | WO 2015/161165 | | 10/2015 |
| WO | WO 2016/103254 | | 6/2016 |
| WO | WO2016103254 | * | 6/2016 |
| WO | WO2016141056 | * | 9/2016 |
| WO | WO2016153347 | * | 9/2016 |
| WO | WO2016209802 | * | 12/2016 |
| WO | WO 2018/148785 | | 8/2018 |
| WO | WO 2018/148786 | | 8/2018 |
| WO | WO 2018/148787 | | 8/2018 |
| WO | WO 2018/165078 | | 9/2018 |

OTHER PUBLICATIONS

ChemicalBook.com [online], "CAS # 541-02-6, Decamethylcyclopentasiloxane," available on or before Sep. 3, 2016 via Internet Archive: Wayback Machine URL: <https://web.archive.org/web/20160903205752/https://www.chemicalbook.com/CASEN_541-02-6.htm>, retrieved on Jan. 4, 2022, URL <https://www.chemicalbook.com/CASEN_541-02-6.htm>, 4 pages.
ChemicalBook.com [online], "CAS # 556-67-2, Octamethylcyclotetrasiloxane," available on or before Mar. 14, 2016, via Internet Archive: Wayback Machine URL <https://web.archive.org/web/20160314105121/https://www.chemicalbook.com/CASEN_556-67-2.htm>, retrieved on Jan. 4, 2022, <https://www.chemicalbook.com/CASEN_556-67-2.htm>, 4 pages.
Extended European Search Report in European Appln No. 19743296.6, dated Nov. 10, 2021, 10 pages.
International Preliminary Report on Patentability in International Appln. No. PCT/AU2019/050051, dated Aug. 6, 2020, 11 pages.
International Search Report and Written Opinion in International Appln. No. PCT/AU2019/050051, dated Apr. 3, 2019, 27 pages.
International Search Report and Written Opinion in International Appln, No. PCT I AU2018/050044, dated Mar. 28, 2018, 9 pages.
Kupczyk et al., "Cannabinoid system in the skin—a possible target for future therapies in dermatology," Experimental dermatology, Aug. 2009, 18(8):669-79.

(Continued)

*Primary Examiner* — Paul V Ward
(74) *Attorney, Agent, or Firm* — Fish & Richardson P.C.

(57) ABSTRACT

A treatment regime for use in the treatment or prevention of dermatitis and inflammatory skin conditions, said regime comprising the administration of: a) between 50 mg and 3000 mg of a topical liquid or gel composition comprising between 1% w/w and 15% w/w cannabinoid, wherein the cannabinoid is dissolved in the liquid or gel composition.

10 Claims, No Drawings

(56) References Cited

OTHER PUBLICATIONS

Mechoulam et al., "A Total synthesis of dl-Δ1-tetrahydrocannabinol, the active constituent of hashish," Journal of the American Chemical Society, Jul. 1965, 87(14): 3273-3275.
Mechoulam et al., "Cannabidiol: An Overview of Some Pharmacological Aspects," J Clin Pharma., Nov. 2002, 42(S1):11S-19S.
No Author, "Safety Assessment of Alkyl PEG/PPG Ethers as Used in Cosmetics," Cosmetic Ingredient Review (CIR) Expert Panel 2013, dated Jun. 20, 2013 [retrieved on Nov. 18, 2020], retrieved from URL <www.cir-safety.org/sites/default/files/PEGPPG062013tent.pdf>, 37 pages.
Petrzilka et al., "Synthese von Haschisch-Inhaltsstoffen. 4. Mitteilung†," Helv Chim Acta., 1969, 52(4):1102-1134 (English Abstract).
Reisine and Pasternak, "Opioid Analgesics and Antagonists," The Pharmacological Basis of Therapeutics, Goodman and Gilman, 1996, 9th Edition, Chapter 23, pp. 521-555.
Stinchcomb et al., "Human skin permeation of [Delta]<8>-tetrahydrocannabinol, cannabidiol and cannabinol," Journal of Pharmacy And Pharmacology—JPP, Mar. 2004, 56(3):291-297.

\* cited by examiner

CANNABINOID DOSING REGIME FOR DERMATITIS AND INFLAMMATORY SKIN CONDITIONS

CROSS REFERENCE TO RELATED APPLICATION

This application is a national phase application under 35 U.S.C. § 371 of PCT International Application number PCT/AU2019/050051, filed Jan. 24, 2019, which claims the benefit of priority under 35 U.S.C. § 119(e) to Australian Patent Application No. 2018900226, filed Jan. 24, 2018, U.S. Application No. 62/621,225, filed Jan. 24, 2018, Australian Patent Application No. 2018903600 filed Sep. 25, 2018 and U.S. Application No. 62/736,052, filed on Sep. 25, 2018, the disclosures of which are incorporated herein in their entirety.

TECHNICAL FIELD

A topical dosing regimen for the treatment or prevention of dermatitis and inflammatory skin conditions using cannabinoids.

BACKGROUND ART

Most mammalian skin, including human skin, comprises three layers: (i) an epidermis layer; (ii) a dermis layer; and (iii) a hypodermis layer. The epidermis itself is made up of two layers, the outer stratum corneum and the inner epidermal basal layer.

The majority of skin conditions involve inflammation triggered by some insult to the skin. Keratinocytes respond quickly to environmental stimuli (e.g., UV radiation (UVR), allergens, irritants or physical damage) by producing a variety of inflammatory mediators, including cytokines (e.g., IL-I, TNF-alpha, and IL-6) and chemokines (e.g., IL-8). One of the most active inflammatory mediators is PGE-2 (Prostaglandin E2) and, of course, many topical dermatology drugs have been designed to lower levels of PGE-2. The fibroblasts in the dermis also produce PGE-2 along with a variety of chemokines, cytokines and matrix destroying enzymes such as collagenase (MMP-I).

Eczema, also known as dermatitis, is a general term for many types of skin conditions that involve inflammation. Atopic dermatitis is the most common of the many types of eczema. Several other forms have very similar symptoms. Some of the diverse types of eczema are listed and briefly described below.

Atopic dermatitis is a chronic skin disease wherein the skin becomes extremely itchy and inflamed, causing redness, swelling, cracking, weeping, crusting, and scaling. Atopic dermatitis most often affects infants and young children, but it can continue into adulthood or first show up later in life. Onset after age 30 is less common and often occurs after exposure of the skin to harsh conditions. In most cases, there are periods of time when the disease is worse, called exacerbations or flares, which are followed by periods when the skin improves or clears up entirely, called remissions. The cause of atopic dermatitis is unknown, but the disease seems to result from a combination of genetic and environmental factors. Atopic dermatitis is very common and affects males and females equally and accounts for 10 to 20% of all referrals to dermatologists; more than 15 million people in the United States have symptoms of the disease. People who live in urban areas and in climates with low humidity seem to be at an increased risk for developing atopic dermatitis.

Dermatitis is also an increasing problem in animals, particularly domestic animals such as pets (dogs, cats). Dogs, for the most part, tend to remain in the cutaneous stage of the atopic disease. Similarly to humans, atopic dermatitis (AD) in dogs is becoming increasingly common.

Contact eczema is a localized reaction that includes redness, itching, and burning where the skin has come into contact with an allergen (an allergy-causing substance) or with an irritant such as an acid, a detergent (soap, bodywash), or other chemical.

Allergic contact eczema is a red, itchy, weepy reaction where the skin has come into contact with a substance that the immune system recognizes as foreign, such as poison ivy or certain preservatives in creams and lotions.

Seborrheic eczema is a form of skin inflammation of unknown cause but which is associated with a certain type of yeast that lives on the skin. Seborrheic eczema presents as yellowish, oily, scaly patches of skin on the scalp, face, and occasionally other parts of the body (called cradle cap in infants).

Nummular eczema is coin-shaped patches of irritated skin-most commonly on the arms, back, buttocks, and lower legs-that may be crusted, scaling, and extremely itchy.

Neurodermatitis is scaly patches of skin on the head, lower legs, wrists, or forearms caused by a localized itch (such as an insect bite) that becomes intensely irritated when scratched.

Stasis dermatitis is a skin irritation on the lower legs, generally related to circulatory problems.

Dyshidrotic eczema is irritation of the skin on the palms of hands and soles of the feet characterized by clear, deep blisters that itch and burn.

Radiation therapy can have some unpleasant side effects which include inflammation of the skin and radiation dermatitis. Specific side effects of radiotherapy, both acute and chronic, depend on the part of the body being treated as well as the dose given. In general, the first change is a reddening of the skin, resembling sunburn. In many patients this is all that is experienced. However, in most patients the burn can be severe and in many cases equivalent to second degree burns. Like sunburn, the involved area is often sensitive and even painful to the touch. In addition, the overlying skin may break down and the area may remain open until several days to weeks after the course of radiation is completed. Once the course of radiotherapy is completed, the redness will gradually go away and any open areas normally will heal. However, the skin in this area will most likely develop features of aged skin including pronounced wrinkling, skin thinning, stiffness and/or dryness, as well as possible pigmentation changes.

Most of the current treatment options for radiation dermatitis involve the use of emollients or aloe gels in an attempt to keep the skin moisturized. However, although moisturization helps the skin from drying out, it does not reduce the pain or redness, which are caused by inflammation.

Rosacea is a vascular, inflammatory skin disorder that affects approximately 5% of the population and is characterized by frequent periods of facial redness or flushing caused by over-active capillaries. Over time, this chronic state of skin inflammation gives rise to a variety of rosacea symptoms. Rosacea is sometimes characterized mistakenly as adult-acne because patients present with a reddened face and acne-like symptoms. However, individuals affected with this skin disease also may have persistent redness with accompanying pain and itching in areas such as the forehead, chin, nose, ears, chest and back. As the disease progresses, small blood vessels and tiny pimples (called papules or pustules) begin to appear on and around the reddened area. In severe cases rosacea can affect the eyes (ocular rosacea) and cause disfigurement of the nose (rhynophyma). In addition to the physical symptoms associated with rosacea, patients also suffer significant psychological and social problems if left untreated. The main form of rosacea is erythrotelangiectatic rosacea (also known as erythematotelangiectatic rosacea or vascular rosacea).

Four rosacea subtypes exist, and a patient may have more than one subtype:
  i) Erythrotelangiectatic rosacea exhibits permanent redness (erythema) with a tendency to flush and blush easily. It is also common to have small, widened blood vessels visible near the surface of the skin (telangiectasias) and possibly intense burning, stinging, or itching. People with this type often have sensitive skin. Skin can also become very dry and flaky. In addition to the face, signs can also appear on the ears, neck, chest, upper back, and scalp.
  ii) Papulopustular rosacea presents with some permanent redness with red bumps (papules); some pus-filled pustules can last 1-4 days or longer. This subtype is often confused with acne.
  iii) Phymatous rosacea is most commonly associated with rhinophyma, an enlargement of the nose. Signs include thickening skin, irregular surface nodularities, and enlargement. Phymatous rosacea can also affect the chin (gnathophyma), forehead (metophyma), cheeks, eyelids (blepharophyma), and ears (otophyma). Telangiectasias may be present.
  iv) Ocular rosacea, where affected eyes and eyelids may appear red due to telangiectasias and inflammation, and may feel dry, irritated, or gritty. Other symptoms include foreign body sensations, itching, burning, stinging, and sensitivity to light. Eyes can become more susceptible to infection. About half of the people with subtypes 1-3 also have eye symptoms. Blurry vision and vision loss can occur if the cornea is affected.

Cannabinoids have been proposed as a treatment for skin conditions such as acne. However, the amount of active agent in the available topical creams is usually very low, and there is little evidence that a therapeutically useful dose is being provided to the user.

It is against this background that the present invention has been developed. The present invention seeks to provide a high dosage composition of cannabinoids for topical use to treat or prevent dermatitis and inflammatory skin conditions, or to provide the consumer with a useful therapeutic or commercial choice.

The previous discussion of the background art is intended to facilitate an understanding of the present invention only. The discussion is not an acknowledgement or admission that any of the material referred to is or was part of the common general knowledge as at the priority date of the application.

SUMMARY OF INVENTION

In accordance with the present invention, there is provided a regime for use in the treatment or prevention of dermatitis and inflammatory skin conditions, said regime comprising the administration of:
  a) between 50 mg and 3000 mg of a topical composition comprising between 1% w/w and 15% w/w cannabinoid to the skin of a subject in need of such treatment or prevention.

Preferably, the composition comprises between 2% w/w and 7% w/w cannabinoid, more preferably 4% w/w.

Preferably, the composition of the treatment regime is administered to the skin between 1 and 5 times per day, more preferably once or twice per day.

Preferably, the composition of the treatment regime delivers between 20 mg and 400 mg of cannabinoid per administration, more preferably 90 mg of cannabinoid per administration.

Preferably, the total daily dose applied to the skin is between 20 mg and 2000 mg cannabinoid, more preferably 180 mg.

The subject to which the treatment regime is applied may be any mammal, for example a human, ape, ovine, bovine, caprine, canine, feline, rodent etc. Most preferably, the subject to which the treatment regime is applied is a human, cat or dog.

The present invention further provides a method for treating or preventing dermatitis and inflammatory skin conditions, said method comprising the administration of:
  a) between 50 mg and 3000 mg of a topical composition comprising between 1% w/w and 15% w/w cannabinoid to the skin of a subject in need of such treatment or prevention.

The present invention further provides for the use of between 50 mg and 3000 mg of a topical composition comprising between 1% w/w and 15% w/w cannabinoid for the treatment or prevention of dermatitis and inflammatory skin conditions in a subject in need of such treatment or prevention.

The present invention further provides for the use of between 1% w/w and 15% w/w cannabinoid for the manufacture of a topical composition for the treatment or prevention of dermatitis and inflammatory skin conditions, wherein between 50 mg and 3000 mg of the topical composition is administered to the skin of a subject in need of such treatment or prevention.

The present invention further provides for the manufacture of a topical composition comprising between 1% w/w and 15% w/w cannabinoid for use in the treatment or prevention of dermatitis and inflammatory skin conditions, wherein between 50 mg and 3000 mg of the topical composition is administered to the skin of a subject in need of such treatment or prevention.

The present invention further provides a topical composition comprising between 1% w/w and 15% w/w cannabinoid for use in the treatment or prevention of dermatitis and inflammatory skin conditions, wherein between 50 mg and 3000 mg of the topical composition is administered to the skin of a subject in need of such treatment or prevention.

DESCRIPTION OF INVENTION

Detailed Description of the Invention

The present invention is based on the finding that the amount of cannabinoids in the available topical creams for inflammatory skin diseases treatment is usually very low, and there is little evidence that a therapeutically useful dose is being provided to the user. The average topical cannabinoid cream is labelled to contain between about 300 mg and 750 mg of cannabinoid per 120 mL jar of cream, which if the labelling is correct, provides an average dose, once applied to the skin, of about 5 mg to 15 mg per dose.

The term cannabinoid includes compounds which interact with the cannabinoid receptor and various cannabinoid mimetics, such as certain tetrahydropyran analogs (e.g., $\Delta^9$-tetrahydrocannabinol, $\Delta^8$-tetrahydro-cannabinol, 6,6,9-trimethyl-3-pentyl-6H-dibenzo [b,d]pyran-1-ol, 3-(1,1-dimethylheptyl)-6,6a,7,8,10,10a-hexahydro-1-hydroxy-6,6-dimethyl-9H-dibenzo[b,d]pyran-9-one, (−)-(3S,4S)-7-hydroxy-Δ6-tetrahydrocannabinol-1,1-dimethylheptyl(+)-(3S,4S)-7-hydroxy-Δ6-tetrahydrocannabinol-1,1-dimethylheptyl, 11-hydroxy-$\Delta^9$-tetrahydrocannabinol, and Δ8-tetrahydrocannabinol-11-oic acid)); certain piperidine analogs (e.g., (−)-(6S,6aR,9R,10aR)-5,6,6a,7,8,9,10,10a-octahydro-6-methyl-3-[(R)-1-methyl-4-phenylbutoxy]-1,9-phenanthridinediol-1-acetate)); certain aminoalkylindole analogs (e.g., (R)-(+)-[2,3-dihydro-5-methyl-3-(-4-morpholinylmethyl)-pyrrolo[1,2,3-de]-1,4-benzoxazin-6-yl]-1-naphthalenyl-methanone); and certain open pyran ring analogs (e.g., 2-[3-methyl-6-(1-methylethenyl)-2-cyclohexen-1-yl]-5-pentyl-1,3-benzenediol and 4-(1,1-dimethylheptyl)-2,3'-dihydroxy-6'alpha-(3-hydroxypropyl)-1',2',3',4',5',6'-hexahydrobiphenyl).

Cannabidiol, as used herein, refers to 2-[3-methyl-6-(1-methylethenyl)-2-cyclohexen-1-yl]-5-pentyl-1,3-benzenediol. The synthesis of cannabidiol is described, for example, in Petilka et al., *Helv. Chim. Acta,* 52: 1102 (1969) and in Mechoulam et al., *J. Am. Chem. Soc.,* 87:3273 (1965), which are hereby incorporated by reference Identification of the main cannabinoid receptors (CB1 and CB2), their endogenous lipid ligands (endocannabinoids), biosynthetic pathways and metabolizing enzymes (collectively termed the ECS), coupled with the discovery and/or rational design of numerous exogenous ligands for CB receptors, has triggered an exponential growth in studies exploring the continuously growing regulatory functions of this newly discovered physiological system both in health and disease.

The most extensively studied endocannabinoids are anandamide (N arachidonoylethanolamine, AEA) and 2-arachidonoylglycerol (2-AG). Multiple pathways are involved in synthesis and cellular uptake of these lipid mediators. The most common degradation pathways for AEA and 2-AG are the fatty acid amid hydrolase (FAAH) and monoacylglycerol lipase (MAGL) enzyme. Endocannabinoids, similar to $\Delta^9$-tetrahydrocannabinol (THC; the main active ingredient of the plant *Cannabis sativa*), predominantly exert their physiological effects via two main G-protein-coupled cannabinoid receptors; however, numerous additional signalling mechanisms and receptor systems (e.g. transient receptor potential cation channel, subfamily V, member 1; TRPV1) might also be involved. Initially, the CB1-mediated effects were described centrally and CB1 receptors were thought to be restricted to the central nervous system, whereas CB2 was first identified at the periphery in immune cells.

It is considered that CBD may:
inhibit hyperproliferation of keratinocytes;
exert universal anti-inflammatory actions such as:
  decrease primed T-cell activity and also inhibit subsequent B-cell response;
  suppress multiple T-cell populations and inhibit general T-cell activation;
  decrease concentrations of pro-inflammatory mediators and also increase the release of anti-inflammatory cytokines;
  inhibit the effects of IFN-γ and/or decrease IFN-γ levels;
  inhibit the migration, proliferation and cell maturation processes involved in Th17, Th1, and Th2 immune responses; and
have direct antioxidant effects.

Without being held to any theory, we believe that the mode of action of CBD for inflammatory skin diseases involves the suppression of mediators of inflammatory responses. There is a physiological regulatory function of the endocannabinoid system (ECS) in proliferation, differentiation, apoptosis and cytokine, mediator and hormone production of various cell types of the skin and appendages (e.g. hair follicle, sebaceous gland).

In vitro studies have shown CBD to stimulate the human vanilloid receptor type 1 (VR1) and to inhibit anandamide (an endogenous CBD neurotransmitter). These findings have suggested a mode of action for the anti-inflammatory properties of CBD. In vivo studies with intravenous administration of CBD in sensitized guinea-pigs reduced airway obstruction, indicating a potential role of CBD in reducing immune-induced inflammatory reactions. Similarly, CBD injected into rats attenuated cardiac inflammation.

Treatment Regime

Inflammatory skin conditions are the most common problem in dermatology. They come in many forms, from occasional rashes accompanied by itching and redness to chronic conditions such as dermatitis (eczema), rosacea, seborrheic dermatitis, and psoriasis. However, they are all linked by one common factor, inflammation. It has been found that the inflammatory markers (cytokines) produced by skin and immune cells that are required for the development of an inflammatory response, such as atopic dermatitis and radiation dermatitis. The present invention comprises active agents, in the form of cannabinoids, that suppress the production of a variety of inflammatory responses in cultured skin cells (keratinocytes and fibroblasts), and immune cells (monocytes and T-lymphocytes) and in intact living skin. As a result of blocking these inflammatory processes in the skin, the present compounds in the form of cannabinoids are able to effectively reduce or eliminate a variety of inflammatory symptoms that occur with common skin problem (see Kupczyk et al (2009) *Cannabinoid system in the skin—a possible target for future therapies in dermatology* Exp Dermatol. 18(8):669-79

High concentrations of dissolved cannabinoids, including cannabidiol (as opposed to solid cannabinoids) are expected to be advantageous in terms of enhancing the relevant extent of delivery into the skin, particularly the epidermis (including the epidermal basal layer), with some penetration into the dermis. It is thought that the high concentration of dissolved cannabinoids on the outer surface of the skin causes a concentration gradient that enhances penetration of the cannabinoid into the skin, particularly the epidermis and the dermis.

In contrast to the prior art, the present invention provide a regime for use in the treatment or prevention of dermatitis and inflammatory skin conditions, said regime comprising the administration of:
  a) between 50 mg and 3000 mg of a topical composition comprising between 1% w/w and 15% w/w cannabinoid to the skin of a subject in need of such treatment or prevention.

The subject to which the treatment regime is applied may be any mammal, for example a human, ape, ovine, bovine, caprine, canine, feline etc. Most preferably, the subject to which the treatment regime is applied is a human, cat or dog.

Preferably the topical composition comprising between 1% w/w and 15% w/w cannabinoid is a liquid or gel composition.

Preferably, an amount of between 50 mg and 3000 mg, between 50 mg and 2000 mg, between 50 mg and 1000 mg, between 50 mg and 500 mg, between 50 mg and 400 mg, between 50 mg and 300 mg, between 50 mg and 200 mg, between 50 mg and 100 mg of the composition may be administered to the skin of the subject in each administration. For example, 50 mg, 100 mg, 200 mg, 300 mg, 400 mg, 500 mg, 600 mg, 700 mg, 800 mg, 900 mg, 1000 mg, 1500 mg, 2000 mg, 2500 mg or 3000 mg of the composition may be administered to the skin of the subject in each administration. Preferably an amount of about 100 mg is administered to the skin of the subject in each administration.

Preferably, an amount of between 50 mg and 3000 mg, between 50 mg and 2000 mg, between 50 mg and 1000 mg, between 50 mg and 500 mg, between 50 mg and 400 mg, between 50 mg and 300 mg, between 50 mg and 200 mg, between 50 mg and 100 mg of the composition may be administered to the face of the subject in each administration. For example, 50 mg, 100 mg, 200 mg, 300 mg, 400 mg, 500 mg, 600 mg, 700 mg, 800 mg, 900 mg, 1000 mg, 1500 mg, 2000 mg, 2500 mg or 3000 mg of the composition may be administered to the face of the subject in each administration. Preferably an amount of about 100 mg is administered to the face of the subject in each administration.

Preferably, an amount of between 50 mg and 3000 mg, between 50 mg and 2000 mg, between 50 mg and 1000 mg, between 50 mg and 500 mg, between 50 mg and 400 mg, between 50 mg and 300 mg, between 50 mg and 200 mg, between 50 mg and 100 mg of the composition may be administered to 565 $cm^2$ of skin of the subject in each administration. For example, 50 mg, 100 mg, 200 mg, 300 mg, 400 mg, 500 mg, 600 mg, 700 mg, 800 mg, 900 mg, 1000 mg, 1500 mg, 2000 mg, 2500 mg or 3000 mg of the composition may be administered to 565 $cm^2$ of skin of the subject in each administration. Preferably an amount of about 100 mg is administered to 565 $cm^2$ of the subject in each administration.

Preferably the composition comprises between 1% w/w and 15% w/w cannabinoid, between 1% w/w and 14% w/w, between 1% w/w and 13% w/w, between 1% w/w and 12% w/w, between 1% w/w and 11% w/w, between 1% w/w and 10% w/w, between 1% w/w and 9% w/w, between 1% w/w and 8% w/w, between 1% w/w and 7% w/w, between 1% w/w and 6% w/w, between 1% w/w and 5% w/w, between 2% w/w and 5% w/w, between 2% w/w and 4% w/w, between 3% w/w and 5% w/w, between 4% w/w and 5% w/w cannabinoid. For example, the composition may comprise 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, or 15% w/w cannabinoid In certain embodiments, the concentration of cannabinoid in the topical composition of the invention may be selected from the group consisting of: at least 2% w/w, at least 3% w/w, at least 4% w/w, at least 5% w/w, at least 6% w/w, at least 7% w/w, at least 8% w/w, at least 9% w/w, at least 10% w/w, at least 11% w/w, at least 12% w/w, at least 13% w/w, at least 14% w/w, and at least 15% w/w.

In certain embodiments, the concentration of cannabinoid in the topical composition may be within a range with a lower limit selected from the group consisting of: 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, and 15% w/w; and an upper limit selected from the group consisting of: 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w and 15% w/w.

More preferably, the concentration of cannabinoid in the topical composition is 4% w/w.

Preferably, the composition of the treatment regime delivers between 20 mg and 400 mg of cannabinoid per administration. For example, the composition of the treatment regime deliver may between 20 mg and 400 mg, 20 mg and 35000 mg, 20 mg and 300 mg, 20 mg and 250 mg, 20 mg and 200 mg, 20 mg and 1500 mg, 20 mg and 100 mg, 20 mg and 50 mg, 30 mg and 100 mg, 40 mg and 100 mg, 50 mg and 100 mg, 60 mg and 100 mg, 70 mg and 100 mg, 80 mg and 100 mg of cannabinoid per administration.

In certain embodiments, the composition of the treatment regime delivers an amount of cannabinoid per administration with a lower limit selected from the group consisting of: 20 mg, 30 mg, 40 mg, 50 mg, 60 mg, 70 mg, 80 mg, 90 mg, 100 mg, 110 mg, 120 mg, 130 mg, 140 mg, 150 mg, 200 mg, 250 mg, 300 mg and 350 mg; and an upper limit selected from the group consisting of: 30 mg, 40 mg, 50 mg, 60 mg, 70 mg, 80 mg, 90 mg, 100 mg, 110 mg, 120 mg, 130 mg, 140 mg, 150 mg, 200 mg, 250 mg, 300 mg, 350 mg and 400 mg.

More preferably, the amount of cannabinoid per administration is 90 mg.

In accordance with certain embodiments, the composition is applied to the affected area regularly until relief is obtained. In one preferred embodiment, the composition is administered to the skin of the patient in need of such treatment using a dosing regimen selected from the group consisting of: every hour, every 2 hours, every 3 hours, once daily, twice daily, three times daily, four times daily, five times daily, once weekly, twice weekly, once fortnightly and once monthly. However, other application schedules may be utilized in accordance with the present invention. Preferably, the composition of the treatment regime is administered to the skin between 1 and 5 times per day, more preferably once or twice per day.

Preferably the total daily dose applied to the skin by administration of the topical composition is between 20 mg and 2000 mg cannabinoid, preferably 20 mg and 2000 mg, 50 mg and 1500 mg, 20 mg and 200 mg, 100 mg and 1000 mg, 150 mg and 500 mg, 200 mg and 500 mg, 200 mg and 400 mg of cannabinoid.

In certain embodiments, the total daily dose of cannabinoid applied to the skin by administration of the topical composition has a lower limit selected from the group consisting of: 20 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 200 mg, 210 mg, 220 mg, 230 mg, 240 mg, 250 mg, 260 mg, 270 mg, 280 mg, 290 mg, 300 mg, 320 mg, 350 mg, 400 mg, 500 mg, 600 mg, 700 mg, 800 mg, 900 mg, 1000 mg, 1500 mg and 1900 mg; and an upper limit selected from the group consisting of: 30 mg, 50 mg, 70 mg, 100 mg, 150 mg, 200 mg, 210 mg, 220 mg, 230 mg, 240 mg, 250 mg, 260 mg, 270 mg, 280 mg, 290 mg, 300 mg, 320 mg, 350 mg, 400 mg, 500 mg, 600 mg, 700 mg, 800 mg, 900 mg, 1000 mg, 1500 mg and 2000 mg.

Most preferably, the total daily dose of cannabinoid applied to the skin by administration of the topical composition is 180 mg.

Thus in relation to the compositions of the present invention, preferably:
  an amount of between 50 mg and 3000 mg of the composition is administered to the skin;
  the administered composition contains between 1% and 15% cannabinoid;

the administered composition delivers between 20 mg and 400 mg cannabinoid;

the composition is administered between 1 and 5 times per day; and the total daily dose applied to the skin is between 20 mg and 2000 mg cannabinoid.

More preferably:

an amount of between 100 mg and 120 mg of the composition is administered to the skin;

the administered composition contains between 3% and 5% cannabinoid;

the administered composition delivers between 80 mg and 120 mg cannabinoid;

the composition is administered one or two times per day; and the total daily dose applied to the skin is between 150 mg and 350 mg cannabinoid.

Most preferably:

an amount of between 100 mg and 120 mg of the composition is administered to the skin;

the administered composition contains 4% cannabinoid;

the administered composition delivers 90 mg cannabinoid;

the composition is administered one or two times per day; and the total daily dose applied to the skin is 180 mg cannabinoid.

High concentrations of cannabinoids delivered to the skin are expected to be advantageous in terms of enhancing the relevant extent of delivery into the skin, particularly the epidermis (including the epidermal basal layer), with some penetration into the dermis. It is thought that the high concentration of cannabinoids on the outer surface of the skin causes a concentration gradient that enhances penetration of the cannabinoid into the skin, particularly the epidermis and the dermis.

In order to achieve local distribution for the treatment of inflammatory skin diseases, it is advantageous for the majority of the cannabinoid, such as cannabidiol (CBD), to penetrate into the epidermis and preferably remain there, and for some cannabinoid to further penetrate to the dermis and the hypodermal layer to be absorbed systemically. In such a case, the cannabidiol would concentrate mainly in the epidermis, thus maximizing its local effect. Not only does the localized effect increase the potential therapeutic benefit, it potentially lessens the frequency and severity of any potential side-effects associated with systemic cannabinoid administration, because the amount of active compound circulating in the patient is reduced.

Treatment and Prevention of Dermatitis and Inflammatory Skin Conditions

In certain embodiments the topical application of cannabinoid, such as cannabidiol, by way of the compositions of the present invention is expected to reduce the incidence and/or severity of inflammatory skin diseases. Therapeutic effects of the present invention include, but are not limited to, reduction in redness, itch, pain or irritation, a reduction in blisters or pustules, a reduction in infection, a reduction of swelling, cracking, weeping, crusting, and scaling and/or a general decrease in inflammation.

The terms inflammatory skin diseases and dermatitis and inflammatory skin conditions are used interchangeably.

In certain embodiments, the topical application of cannabinoid, such as cannabidiol, by way of the compositions of the present invention is expected to improve the symptoms of inflammatory skin diseases.

The term "improve" is used to convey that the present invention changes either the appearance, form, characteristics and/or the physical attributes of the tissue to which it is being provided, applied or administered. The change in form may be demonstrated by any of the following alone or in combination: enhanced appearance of the skin; decreased inflammation of the skin, prevention of inflammation or blisters, decreased spread of blisters, decreased ulceration of the skin, decreased redness, reduction of scarring, reduction in lesions, healing of blisters, reduced skin thickening, closure of wounds and lesions, a reduction in symptoms including, but not limited to, pain, inflammation, itching, milia or other symptoms associated with inflammatory conditions or the like.

A primary advantage of the present invention is expected to be the improvement in the condition of the skin without the typical side effects of conventional therapies. The potential for the present invention is widespread, and the topical application of cannabinoids shows promise as an exciting new method of inflammatory skin disease treatment.

It is expected that treatment of dermatitis and inflammatory skin conditions in accordance with embodiments of the present invention results in improved healing of the skin. For example, when used in the treatment of inflammatory skin diseases, swollen, cracked or scaled skin is which is treated is expected to heal more quickly and/or completely, compared to when left untreated.

When administered in accordance with the present invention, treatment is expected to result in one or more therapeutic effects. Therapeutic effects in the affected area include, but are not limited to, reduction in redness, itch, pain or irritation, the number and severity of the dermatitis lesions, a reduction in infection, a reduction of swelling, cracking, weeping, crusting, and scaling and/or a general decrease in inflammation. One or more of these therapeutic effects are expected to be observed when treatment in accordance with the present invention is made to any of the suitable conditions.

The present invention therefore provides a method for treating or preventing dermatitis and inflammatory skin conditions, said method comprising the administration of:

a) between 50 mg and 3000 mg of a topical composition comprising between 1% w/w and 15% w/w cannabinoid to the skin of a subject in need of such treatment or prevention.

Preferably the topical composition comprising between 1% w/w and 15% w/w cannabinoid is a liquid or gel composition. Preferably the composition is non-aqueous.

The subject to which the treatment regime is applied may be any mammal, for example a human, ape, ovine, bovine, caprine, canine, feline etc. Most preferably, the subject to which the treatment regime is applied is a human, cat or dog.

The present invention further provides for the use of between 50 mg and 3000 mg of a topical composition comprising between 1% w/w and 15% w/w cannabinoid for the treatment or prevention of dermatitis and inflammatory skin conditions in a subject in need of such treatment or prevention.

The present invention further provides for the use of between 1% w/w and 15% w/w cannabinoid for the manufacture of a topical composition for the treatment or prevention of dermatitis and inflammatory skin conditions, wherein between 50 mg and 3000 mg of the topical composition is administered to the skin of a subject in need of such treatment or prevention.

In one aspect, the present invention is directed to methods of treating or preventing dermatitis and inflammatory skin conditions using topical cannabinoids, including cannabidiol. In accordance with certain embodiments, a topical composition of the invention containing cannabinoids such as cannabidiol, is preferably applied topically to an area which is affected by the inflammatory skin disease. Preferably, the application of cannabinoid in accordance with certain embodiments results in reduction in redness, itch, pain or irritation, a reduction in blisters or pustules, a reduction in infection, less breakdown and loss of collagen and elastin in the skin, a reduction of swelling, cracking, weeping, crusting, and scaling and/or a general decrease in inflammation.

Thus in relation to the methods of the present invention, preferably:
- an amount of between 50 mg and 3000 mg of the composition is administered to the skin;
- the administered composition contains between 1% and 15% cannabinoid;
- the administered composition delivers between 20 mg and 400 mg cannabinoid;
- the composition is administered between 1 and 5 times per day; and
- the total daily dose applied to the skin is between 20 mg and 2000 mg cannabinoid.

More preferably:
- an amount of between 100 mg and 120 mg of the composition is administered to the skin;
- the administered composition contains between 3% and 5% cannabinoid;
- the administered composition delivers between 80 mg and 120 mg cannabinoid;
- the composition is administered one or two times per day; and
- the total daily dose applied to the skin is between 150 mg and 350 mg cannabinoid.

Most preferably:
- an amount of between 100 mg and 120 mg of the composition is administered to the skin;
- the administered composition contains 4% cannabinoid;
- the administered composition delivers 90 mg cannabinoid;
- the composition is administered one or two times per day; and
- the total daily dose applied to the skin is 180 mg cannabinoid.

Unless the context requires otherwise, the phrase "inflammatory skin condition" includes skin diseases and skin disorders, and means conditions that are accompanied by a series of clinical signs and symptoms, such as itch, oedema, erythema and abrasion and are induced by various stimulative factors that cause a series of inflammatory reactions in the skin. In some aspects, the inflammatory skin condition may be characterized by ulceration, inflammation, or blistering of the skin. In some embodiments, the inflammatory skin condition may be characterized by a genetic component, an autoimmune component, a circulatory component or combinations thereof.

In one embodiment, the "inflammatory skin condition" is selected from the list: rosacea, dermatitis (including radiation dermatitis, atopic dermatitis, allergic and irritant contact dermatitis, seborrheic dermatitis, statis dermatitis), erythemas (sunburns), actinic keratitis (including actinic cheilitis), scarring, hyperpigmentation, lupus erythematosus, pemphigoid, hives, eczema, lichen planus, acrodermatitis, dermatomyositis, inflammatory skin conditions resulting from skin infections (including tinea pedis and tinea versicolor, shingles, mouth ulcers (including stomatitis, canker sore), nappy rash, erysipelas, impetigo, cutaneous candidiasis), or inflammation resulting from bites and stings (including bee stings, ant bites, wasp stings, tick bites, flea bites, scabies infections).

In one embodiment, the "inflammatory skin condition" is selected from the list: cutaneous porphyria, sclerodema, epidermolysis bulosa, decubitus ulcers, pressure ulcers, diabetic ulcers, venous stasis ulcers, sickle cell ulcers, ulcers caused by burns, urticaria, dermatitis herpetiform, arthritis, gout, alopecia, carcinomas, miliaria, skin infections, post-operative care of incisions, post-operative skin care following any variety of plastic surgery operations, skin care following radiation treatment, care of dry, cracked or aged skin and skin lines as well as other conditions affecting the skin and having an inflammatory component, symptoms thereof, or a combination thereof. Symptoms treated may include pain, inflammation, redness, itching, scarring, skin thickening, milia, or a combination thereof.

In one embodiment, the "inflammatory skin condition" is selected from the list: dermatological pain, dermatological inflammation, bacterial skin infections, fungal skin infections, viral skin infections, parasitic skin infections, skin neoplasia, skin neoplasms, pruritus, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, pediculosis, creeping eruption, pityriasis rosea, pityriasis rubra pilaris, edematous, erythema multiform, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, purpura, moniliasis, candidiasis, baldness, androgenetic alopecia, Behcet's syndrome, cholesteatoma, Dercum disease, ectodermal dysplasia, gustatory sweating, nail patella syndrome, telogen effluvium, Hailey-Hailey disease, chemical or thermal skin burns, scleroderma, aging skin, wrinkles, sun spots, necrotizing fasciitis, necrotizing myositis, gangrene, scarring, and vitiligo.

In a specific embodiment, the phrase "inflammatory skin condition" means rosacea, radiation dermatitis, erythemas (sunburns), atopic dermatitis, allergic and irritant contact dermatitis, actinic keratitis, scarring, hyperpigmentation, and seborrheic dermatitis or eczema, or other eczemas, or and alopecia areata.

Preferably the inflammatory skin condition is selected from atopic dermatitis or rosacea.

Pharmaceutical Composition

The present invention provides a composition comprising between 1% w/w and 15% w/w cannabinoid for use in the treatment or prevention of dermatitis and inflammatory skin conditions, wherein between 50 mg and 3000 mg of the topical composition is administered to the skin of a subject in need of such treatment or prevention. Preferably the composition is administered to the skin between 1 and 5 times per day and preferably the total daily dose applied to the skin by administration of the topical composition is between 20 mg and 2000 mg cannabinoid.

Preferably there is a therapeutically effective amount of cannabinoid in each topical dose of the composition of the present invention. Therapeutically effective amount means the amount necessary to bring about a therapeutic effect.

Certain embodiments of the present invention comprise any topically acceptable carrier vehicle. Preferred topically acceptable vehicles include but are not limited to gels, ointments, and liquids. Administration of the preferred embodiment is performed in accordance with that mode which is most amenable to the topically acceptable form chosen. For example, gels, lotions, creams and ointments are preferably administered by spreading. The topical composition may or may not contain water, i.e. it may be an aqueous or a non-aqueous composition.

The dilution of the cannabinoid in the topical composition can be an important consideration. The cannabinoid concentration in the composition should be high enough that the patient does not need to wait an excessively long time for the composition to dry. On the other hand, the cannabinoid concentration should be dilute enough that a patient can achieve effective coverage of the affected area. Additionally, the composition could include a component which polymerizes in response to exposure to air or ultraviolet radiation.

The amount of composition to be applied will vary. When the cannabinoid, such as cannabidiol, is administered by spraying a solution of the drug, the total volume in a single dose may be as low as 0.1 ml. When the cannabinoid, such as cannabidiol, is administered in a gel or cream, the total volume may be as high as 3 ml. Conversely, if the inflammatory skin disease comprises scattered lesions, the volume applied to each lesion may be smaller. The carrier selected, and its manner of application, are preferably chosen in consideration of the needs of the patient and the preferences of the administering physician.

In one preferred embodiment, the composition comprises a gel which is preferably administered by spreading the gel onto the affected area. In other preferred embodiments, the composition comprises a liquid, which can be administered by spraying or otherwise applying the liquid onto the affected area.

In certain embodiments, the composition of the invention may be provided in a form selected from the group comprising, but not limited to a liquid, cream or gel. The composition may be a leave-on preparation, or a wash-off preparation. In one preferred form, the composition is a cream or gel. In another preferred form, the composition is a spray. The composition may or may not contain water. Preferably, the composition does not contain water, i.e. it is non-aqueous.

The cannabinoid could be incorporated into a composition with an additional active moiety that is capable of improving the appearance and/or hydration of the skin.

In addition, the composition of the present invention can be used in conjunction with other topically applied analgesic and/or systemically available agents for the treatment of inflammatory skin diseases.

Examples of such analgesic agents include, but are not limited to: morphine, cyclazocine, piperidine, piperazine, pyrrolidine, morphiceptin, meperidine, trifluadom, benzeneacetamine, diacylacetamide, benzomorphan, alkaloids, peptides, phenanthrene and pharmaceutically acceptable salts, prodrugs or derivatives thereof. Specific examples of compounds contemplated by as suitable in the present invention include, but are not limited to morphine, heroin, hydromorphone, oxymorphone, levophanol, methadone, meperidine, fentanyl, codeine, hydrocodone, oxycodone, propoxyphene, buprenorphine, butorphanol, pentazocine and nalbuphine. As used in the context of opioid agents herein, "pharmaceutically acceptable salts, prodrugs and derivatives" refers to derivatives of the opioid analgesic compounds that are modified by, e.g., making acid or base salts thereof, or by modifying functional groups present on the compounds in such a way that the modifications are cleaved, either in routine manipulation or in vivo, to produce the analgesically active parent compound. Examples include but are not limited to mineral or organic salts of acidic residues such as amines, alkali or organic salts of acidic residues such as carboxylic acids, acetate, formate, sulfate, tartrate and benzoate derivatives, etc. Suitable opioid analgesic agents, including those specifically mentioned above, are also described in Goodman and Gilman, ibid, chapter 28, pp. 521-555.

In addition, other active agents may be included in the composition of the present invention, e.g., topically-effective anaesthetics such as xylocaine, cocaine, lidocaine, benzocaine, etc., which may provide a more immediate, if less effective in the long run, level of pain relief until the analgesic agent becomes fully effective.

Still other agents can also be administered, preferably topically, to potentiate the effects of the topically-administered cannabidiol. For example, dextromethorphan, a non-addictive opioid compound, can be co-administered, preferably topically, although parenteral administration is also effective, to enhance the effectiveness of the topically administered agent. Without wishing to be bound by theory, it is believed that dextromethorphan has previously unappreciated analgesic properties in peripheral nerves. Suitable concentrations of dextromethorphan are routinely ascertainable by the skilled worker, and include the normal therapeutic amounts administered parenterally for conventional purposes, e.g., as a cough suppressant, or less, and routinely determinable amounts for topical administration; for example, 1 g of dextromethorphan can be added to a composition disclosed herein to provide additional treatment for inflammatory skin diseases.

In one embodiment, the pharmaceutical composition of the present invention further comprises one or more of the following agents for the treatment of dermatitis and inflammatory skin conditions: salicylic acid; resorcinol; sulfacetamide; urea; imidazoles such as ketoconazole and elubiol; essential oils; alpha-bisabolol; dipotassium glycyrrhizinate; camphor; beta.-glucan; allantoin; feverfew; flavonoids such as soy isoflavones; saw palmetto; chelating agents such as EDTA; lipase inhibitors such as silver and copper ions; hydrolyzed vegetable proteins; inorganic ions of chloride, iodide, fluoride, and their nonionic derivatives chlorine, iodine, fluorine; synthetic phospholipids and natural phospholipids; steroidal anti-inflammatory agents such as hydrocortisone, hydroxyltriamcinolone alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, fluticasone monopropionate, fluticasone furoate, mometasone furoate, budesonide, ciclesonide and salts are prodrugs thereof; nonsteroidal anti-Inflammatory drugs (NSAIDs) such as COX inhibitors, LOX inhibitors, p38 kinase inhibitors including ibuprofen, naproxen, salicylic acid, ketoprofen, hetprofen and diclofenac; analgesic active agents for treating pain and itch such as methyl salicylate, menthol, trolamine salicylate, capsaicin, lidocaine, benzocaine, pramoxine hydrochloride, and hydrocortisone; antibiotic agents such as mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, tetracycline, clindamycin, erythromycin; immunosuppressant agents such as cyclosporine and cytokine synthesis inhibitors, tetracycline, minocycline, and doxycycline, or any combination thereof.

In preferred forms of the invention, the formulation is not a solid formulation, such as a patch or adhesive bandage. In preferred forms of the invention, the composition is a liquid formulation.

It is preferable that the composition concentrates the cannabinoid on the skin. To achieve this, one preferred method is to provide the cannabinoid in a composition comprising a mixture of a volatile solvent and a residual (less volatile) solvent.

Volatile Solvents

By using a volatile solvent, one can achieve much higher, non-crystalline (i.e., in solution), concentrations of cannabinoids. The cannabinoids can be dissolved in much higher concentrations of the volatile solvent, and then once applied to the skin and the volatile solvent has evaporated, the cannabinoids remain on the skin in high concentrations. The volatile solvent may, for example, be a $C_{2-6}$ low molecular weight alcohol such as methanol, isopropanol, propanol, 2-butanol, n-butanol and ethanol. Alternatively, the volatile solvent may be a siloxane. Other suitable volatile solvents will be clear to the skilled reader.

In a preferred form of the invention, the composition comprises a combination of a $C_{2-6}$ low molecular weight alcohol and a siloxane.

Advantageously, in some embodiments, the volatile solvent is a liquid at ambient temperatures. Preferably the volatile solvent is liquid at about 30° C., or less, or at about 25° C. Preferably the level of volatility of the volatile solvent is about the same as that of isopropyl alcohol. Preferably, the boiling point of the volatile solvent is between about 70° C. and 110° C. at atmospheric pressure. Preferably, the boiling point of the volatile solvent is between about 80° C. and 105° C. at atmospheric pressure. Preferably, the boiling point of the volatile solvent is between about 85° C. and 105° C. at atmospheric pressure.

Advantageously, in some embodiments, the volatile solvent is selected from the group consisting of: $C_{2-6}$ alcohols, and combinations thereof. Advantageously, in some embodiments, the volatile solvent is selected from the group consisting of: $C_{2-4}$ alcohols, and combinations thereof. In specific embodiments, the volatile solvent is selected from the group consisting of: ethyl alcohol (or ethanol), n-propanol, isopropyl alcohol, butanol, and combinations thereof. Other volatile solvents will be clear to the skilled reader.

Alternatively, the volatile solvent comprises a siloxane. Preferably, the volatile solvent comprises a non-polymeric siloxane.

In a preferred form of the invention, the siloxane contains from one to eight silicon atoms per molecule. In a preferred form of the invention, the siloxane contains from two to five silicon atoms per molecule. In one embodiment, the siloxane contains two or three silicon atoms.

The siloxanes may have between one and eight methyl groups. In one embodiment, the siloxane is selected from the group consisting of: hexamethyldisiloxane, octamethyltrisiloxane and combinations thereof. These are the most volatile siloxanes, and are thus the most advantageous. Preferably the level of volatility of the siloxane is about the same as that of isopropyl alcohol.

In another embodiment, the siloxane contains 4 or 5 silicon atoms, and is, for example, decamethyltetrasiloxane or dodecamethylpentasiloxane. In another embodiment, the siloxane is a cyclical 4 or 5 silicon atom compound such octamethylcyclotetrasiloxane (CAS #556-67-2) or decamethylcyclopentasiloxane (CAS #541-02-6).

In one form of the invention, the volatile solvent is hexylmethyldisiloxane which is combined with less volatile polymethylsiloxane.

In a preferred form of the invention, the composition comprises a combination of a $C_{2-6}$ low molecular weight alcohol and a non-polymeric siloxane.

In a preferred form of the invention, the cannabinoid is dissolved in the volatile solvent.

In specific embodiments, the relative amount of volatile solvent is selected from the following group: at least 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, 95% w/w or 97% w/w. In specific embodiments, the maximum concentration of the volatile solvent is 50% w/w, 60% w/w, 70% w/w, 80% w/w, 90% w/w, 95% w/w or 97% w/w. The relative amount of volatile solvent may be between 1% w/w and 97% w/w, 10% w/w and 97%, 10% w/w and 90% w/w, 50% w/w and 97% w/w, 50% w/w and 95% w/w.

Preferably, the volatile solvent is provided as 85-95% w/w non-polymeric siloxane and 1-10% wt/wt $C_2$-$C_6$ alcohol.

Residual Solvents

The cannabinoids are preferably kept in a non-crystalline form on the skin after evaporation of the volatile solvent by the addition of a less volatile solvent. This less volatile solvent is called the residual solvent, as it may remain on the skin after evaporation of the volatile solvent to keep the cannabinoid in a non-crystalline state after evaporation of the volatile solvent. Preferably the residual solvent has a low volatility such that less than 5% would evaporate at skin temperature over 24 hours. Preferably, the residual solvent has a chain structure that has a hydrophobic end and a hydrophilic end. Preferably the residual solvent is a liquid at or below 32° C. Preferably the residual solvent dissolves the volatile solvent. Preferably the residual solvent maintains the cannabinoid in non-crystalline form, i.e. in solution, at concentrations of 20% up to 70% w/w cannabinoid.

The purpose of the residual solvent is to act as a solvent for the cannabinoid once the volatile solvent has evaporated. The residual solvent may be a compound from the list comprising: fatty acids, fatty acid alcohols, fatty alcohols, glycols or alkanes, or ethers of any of these. It is preferably a $C_{12-22}$ compound. The residual solvent may comprise a mixture of, for example, alkyl polypropylene glycol/polyethylene glycol ether and/or a fatty acid alcohol and/or a fatty alcohol. In specific embodiments the residual solvent is a $C_{12-22}$ fatty alcohol. In specific embodiments, the residual solvent is a $C_{16-22}$ fatty alcohol. In specific embodiments, the residual solvent is selected from the group consisting of: oleyl alcohol, isostearyl alcohol, isohexadecane, octyldodecyl alcohol, 2-hexyl decyl alcohol. Most preferably the residual solvent is isohexadecane.

In specific embodiments, the relative amount of residual solvent may be selected from the following group: at least 1% w/w, at least 2% w/w, at least 3% w/w, at least 4% w/w, at least 5% w/w, at least 6% w/w, at least 7% w/w, at least 8% w/w, at least 9% w/w, at least 10% w/w, at least 20% w/w, at least 30% w/w, at least 40% w/w, at least 50% w/w. In specific embodiments, the maximum concentration of the residual solvent is 50% w/w. In specific embodiments, the maximum concentration of the residual solvent is 80% w/w. The relative amount of residual solvent may be selected from the following group: between 1% and 80% w/w, between 1% and 50% w/w, between 1% and 40% w/w, between 1% and 30% w/w, between 1% and 20% w/w, between 1% and 10% w/w, between 2% and 80% w/w, between 2% and 50% w/w, between 2% and 20% w/w, between 2% and 10% w/w. Preferably the amount of residual solvent is between 1-10% w/w.

Preferably the amount of residual solvent is sufficient to keep the cannabinoid in a non-crystalline form, i.e. in solution, on the skin after partial or complete evaporation of the more volatile solvent or solvents.

Where the composition comprises a residual solvent and a volatile solvent, the composition comprises a solution of the cannabinoid in the mixture of the volatile solvent and the residual solvent. The composition may consist of a solution of the cannabinoid in the mixture of the volatile solvent and the residual solvent, or comprise a solution of the cannabinoid in the mixture of the volatile solvent and the residual solvent in combination with solid cannabinoid, such as a suspension of solid cannabinoid in a saturated solution of the cannabinoid in the mixture of volatile solvent and residual solvent. In preferred forms of the invention, the composition does not comprise solid cannabinoid.

The total amount of the volatile solvent, and the residual solvent if present, required is sufficient to keep the cannabinoid non-crystalline, i.e. in solution, at room temperature for between about 2-8 hours once the composition is applied to the skin.

The preferred ratio of cannabinoid to siloxane to residual solvent is selected from the range consisting of (w/w %):
between 0.5-20% cannabinoid, between 1-99% siloxane and between 0.1-98.5% residual solvent;
between 5-20% cannabinoid, between 4-70% siloxane and between 1%-70% residual solvent;
between 1-10% cannabinoid, between 20-98% siloxane and between 1-10% residual solvent.

The preferred ratio of cannabinoid to hexamethyldisiloxane to residual solvent is selected from the range consisting of (w/w %):
between 0.5-20% cannabinoid, between 1-99% hexamethyldisiloxane and between 0.1-98.5% residual solvent;
between 5-20% cannabinoid, between 4-70% hexamethyldisiloxane and between 1%-70% residual solvent;
between 1-10% cannabinoid, between 20-98% hexamethyldisiloxane and between 1-10% residual solvent.

As noted above, in highly preferred forms of the invention, the composition comprises 4% w/w of cannabidiol.

Where the composition contains 4% w/w cannabidiol, the composition preferably comprises 85-95% w/w volatile solvent in the form of a non-polymeric siloxane. In a preferred form of the invention, the non-polymeric siloxane comprises two to three silicon atoms per molecule. In a preferred form of the invention, the non-polymeric siloxane is hexamethyldisiloxane.

In a preferred form of the invention, the viscosity of the siloxane, preferably hexamethyldisiloxane, is between 0.5 and 0.7 cSt.

Where the composition contains 4% w/w cannabidiol and 85-95% w/w volatile solvent in the form of a non-polymeric siloxane, the composition optionally further comprises a volatile solvent in the form of a $C_{2-6}$ low molecular weight alcohol at a concentration of 1-10% w/w. In preferred forms of the invention, the concentration is 15% w/w. In preferred forms of the invention, the concentration is 2-4% w/w. In a preferred form of the invention, the $C_{2-6}$ low molecular weight alcohol is an alcohol containing between two and four carbon atoms per molecule. In preferred forms of the invention, the $C_{2-6}$ low molecular weight alcohol is isopropyl alcohol.

Where the composition contains 4% w/w cannabidiol, 85-95% w/w volatile solvent in the form of a non-polymeric siloxane, and 1-10% w/w volatile solvent in the form of a $C_{2-6}$ low molecular weight alcohol, the composition optionally further comprises 1-10% w/w residual solvent in the form of fatty acids, fatty acid alcohols, fatty alcohols, glycols, alkanes, ethers of any of these, and combinations thereof. In a preferred form of the invention, the residual solvent is isohexadecane.

Viscosity Modifier

The present invention may include a viscosity modifier. The viscosity modifier has little effect on the delivery of the active cannabinoid from the composition, but may contribute significantly to patient compliance by improving the tactile qualities of the composition.

In one form of the invention, the viscosity modifier is a silicone fluid. In one form of the invention, the viscosity modifier is a polysiloxane. Where the viscosity modifier is a polysiloxane, the viscosity modifier is preferably a polydimethylsiloxane. Preferably, where the viscosity modifier is a polysiloxane, including a polydimethylsiloxane, the viscosity modifier has a viscosity of between 10,000 and 15,000 cSt, preferably still 11,500 and 13,500 cSt. In a highly preferred form of the invention, the viscosity modifier has a viscosity of approximately 12,500 cSt.

Where the polysiloxane viscosity modifier has a viscosity of between 10,000 and 15,000 cSt, the concentration of the polysiloxane viscosity modifier is preferably between 0.2 and 2% w/w. Preferably still, the concentration of the polysiloxane viscosity modifier is between 0.5 and 1.5% w/w. Preferably still, the concentration of the polysiloxane viscosity modifier is between 0.8 and 1.2% w/w.

The polysiloxane viscosity modifier may be provided in the form of a dimethiconol gum. The dimethiconol gum may be used alone, or in conjunction with another polysiloxane viscosity modifier, such as polydimethylsiloxane. In preferred forms of the invention, the dimethiconol gum is used in conjunction with the polydimethylsiloxane viscosity modifier. Preferably, the concentration of the dimethiconol gum viscosity modifier in the composition is between 3 and 7% w/w. Preferably, the concentration of the dimethiconol gum viscosity modifier in the composition is between 4 and 6% w/w. Preferably, the concentration of the dimethiconol gum viscosity modifier in the composition is between 4.5 and 5.5% w/w.

Such administration is expected to result in enhanced delivery of a cannabinoid, such as cannabidiol, to the epidermis and dermis of the skin, which is expected to be effective in significantly reducing, and therefore treating, acne in patients in need of such treatment.

In one preferred embodiment, the composition is non-aqueous. In another preferred embodiment, the composition does not comprise a preservative.

General

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Those skilled in the art will appreciate that the invention described herein is susceptible to variations and modifications other than those specifically described. The invention includes all such variation and modifications. The invention also includes all of the steps, features, compositions and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The invention described herein may include one or more range of values (e.g. concentration). A range of values will be understood to include all values within the range, including the values defining the range, and values adjacent to the range which lead to the same or substantially the same outcome as the values immediately adjacent to that value which defines the boundary to the range.

EXAMPLES

Further features of the present invention are more fully described in the following description of several non-limiting embodiments thereof. The following Examples are to be construed as merely illustrative and not limitative of the remainder of the disclosure in any way whatsoever. This description is included solely for the purposes of exemplifying the present invention. It should not be understood as a restriction on the broad summary, disclosure or description of the invention as set out above.

Example 1

Techniques for Ascertaining Permeability of Compositions Containing Cannabidiol

Dermatomed skin from a single donor was mounted in a Franz-type diffusion cell (0.55 cm$^2$ receptor fluid exposure surface area) and dosed with 5 ul of CBD formulated in an mixture of a volatile solvent (hexylmethyldisiloxane/polymethylsiloxane—93% w/w), and residual solvent (arlamol E—2% w/w) at a concentration of 5.0% (w/w; 35.5 mg/ml).

Following dosing, receptor phase samples were collected at 4, 10, 24 and 48 hours; after which the study was terminated.

The residual formulation was removed by tape stripping and the epidermis and dermis separated by blunt dissection. The levels of CBD in the epidermis, dermis, and receptor fluid samples were then analyzed using a bioanalytical method with LC-MS/MS detection.

The data showed that skin permeation (i.e., permeation through to the receptor phase of the test system) was negligible, with less than 0.081% (278 ng/cm$^2$) in the receptor phase over the 48-hour exposure period.

The various layers of the skin showed different amounts of absorbed dose over the 48-hour period: epidermal deposition of CBD was 13.17% of the applied dose, while dermal deposition of CBD was 4.54% of the applied dose. The dermis concentration was 8,408 ng/cm$^2$ or 1,933 ng/g of tissue (~1,933 ng/mL) following application of CBD mixture.

These results suggest that the level of systemic exposure for CBD is likely to be very low following topical administration in vivo.

Example 2

A Randomized, Double-Blind, Vehicle-Controlled Study of the Safety, Tolerability and Efficacy of BTX 1204 in Patients with Moderate Atopic Dermatitis The objective of the study is to determine the safety, tolerability and efficacy of BTX 1204 in subjects 12 to 70 years of age with moderate atopic dermatitis (AD).

Methodology:

Number of Subjects: 200 subjects randomized 1:1 (100 subjects to BTX 1204 4% and 100 subjects to Vehicle) will be enrolled.

Diagnosis and Main Criteria for Inclusion:

This study will include males and females between 12 and 70 years of age (inclusive). Subjects will be in good general health without clinically significant disease and have a diagnosis of chronic (≥1 year), stable atopic dermatitis (AD) according to Hanifin and Rajka [Hannifin 1980].

Hanifin and Rajka Diagnostic Criteria for Atopic Dermatitis (AD)

Major criteria: Must have three or more of:
 i) Pruritus
 ii) Typical morphology and distribution
  Flexural lichenification or linearity in adults
  Facial and extensor involvement in infants and children
 iii) Chronic or chronically-relapsing dermatitis
 iv) Personal or family history of atopy (asthma, allergic rhinitis, atopic dermatitis)

Minor criteria: Should have three or more of:
 i) Xerosis
 ii) Ichthyosis, palmar hyperlinearity, or keratosis pilaris
 iii) Immediate (type 1) skin-test reactivity
 iv) Raised serum IgE
 v) Early age of onset
 vi) Tendency toward cutaneous infections (especially S aureus and herpes simplex) or impaired cell-mediated immunity
 vii) Tendency toward non-specific hand or foot dermatitis
 viii) Nipple eczema
 ix) Cheilitis
 x) Recurrent conjunctivitis
 xi) Dennie-Morgan infraorbital fold
 xii) Keratoconus
 xiii) Anterior subcapsular cataracts
 xiv) Orbital darkening xv) Facial pallor or facial erythema
xvi) Pityriasis alba
xvii) Anterior neck folds
xviii) Itch when sweating
xix) Intolerance to wool and lipid solvents
xx) Perifollicular accentuation
xxi) Food intolerance
xxii) Course influenced by environmental or emotional factors
xxiii) White dermographism or delayed blanch Subjects will have:
- ≥5% and ≤30% body surface area (BSA) of AD involvement excluding the scalp and groin;
- an Investigator's Global Assessment (IGA) score of moderate (3) atopic dermatitis on the 5-point IGA (0-4) scale.

For selected photography sites, subject has a target lesion 25 to 200 cm2 in surface area on the trunk, upper extremities or lower extremities with a Baseline Signs of AD score of ≥6 and ≤12.

Subjects should not wash or shave treatable AD lesions within 5 minutes prior to or for 1 hour after application of study medication. Subjects may use bland emollients to manage dry skin areas around, but not overlapping, the treatable AD lesions. Sunscreens may be applied to the skin areas around, but not overlapping, the treatable AD lesions.

In addition, swimming, heavy exercise, or application of sunscreens was prohibited for 4 hours after application of study drug to maximize the time allowed for study drug absorption. Subjects agreed to maintain their regular use of sunscreens, moisturizers, and facial makeup throughout the entire course of the study and not apply sunscreens, moisturizers, or facial makeup within 4 hours prior to, or 1 hour after, study drug application.

Subjects were also instructed to avoid excessive ultraviolet radiation exposure as might be experienced while sunbathing or tanning. Hats, sunglasses, and other protective garments were to be worn to protect the area treated with study drug throughout the study.

Throughout the study, every attempt was made to keep the individual use of concomitant therapies consistent. Medications that could have interfered with the efficacy and/or safety assessments were prohibited.

Test Product, Dose and Mode of Administration:

Each milliliter of the BTX 1204 4% (w/w) Liquid Formulation contains 30.0 mg of CBD. The Vehicle will be identical to the BTX 1204 4% (w/w), but without the CBD. The excipients include hexamethyldisiloxane, silicone gum, polypropylene glycol (PPG) 15 stearyl ether, and isopropyl alcohol (IPA). The solution spreads easily and quickly evaporates leaving the CBD on the skin.

Study drug, active and vehicle, will be supplied in 125 mL multi-dose, metered pumps delivering 0.5 mL per actuation. Each pump will contain approximately 100 mL of study drug. Each subject will apply ~0.7 mL per each 1% BSA per dose. Example: A subject with a BSA of 10% will apply 7 mL of study drug with each dose to cover all the AD lesions (except scalp and groin). This will require 14 actuations of the 0.5 mL pump.

Study drug will be applied directly to the AD lesion and spread to cover the AD lesion and up to 1 cm of the surrounding non-lesional skin. For lesions that cannot be accessed for direct application, study drug will be pumped into the palm of one hand and applied to the AD lesions.

Study drug will be applied twice daily, with the first application of study drug occurring at approximately the same time each the morning and the second application approximately 8 to 12 hours later.

Administration:

A target lesion will be identified based on the inclusion criteria. Measurement of the target lesion and total body surface arearea (BSA) of AD involvement will be obtained.

Baseline photographs of selected sites will be obtained. The Investigator Global Assessment (IGA), Signs of atopic dermatitis (AD) score, body surface area (BSA) of AD, Eczema Area and Severity Index (EASI) score, and changes in pruritus will be measured. Clinical site staff will apply the first dose of study drug. Cutaneous tolerability assessments will be conducted prior to and approximately 15 minutes after the first application.

For all subjects, a complete blood count (CBC), chemistry, and urinalysis will be conducted at the Baseline and Day 85 Visits. The following will be assessed:

- CBC: White blood cell (WBC) count (with automated differential for absolute neutrophils, lymphocytes, monocytes, eosinophils, and basophils), red blood cell (RBC) count, haemoglobin, hematocrit, mean corpuscular volume (MCV), mean corpuscular haemoglobin (MCH), mean corpuscular haemoglobin concentration (MCHC), and platelet count;
- Chemistry: Glucose, albumin, total protein, calcium, sodium, potassium, chloride, $CO_2$ (bicarbonate), blood urea nitrogen (BUN), creatinine, alkaline phosphatase, alanine amino transferase (ALT), aspartate amine transferase (AST), and total bilirubin;
- Urinalysis: Color, clarity, specific gravity, pH, protein, glucose, and leukocyte esterase. If the results are abnormal or further analysis is requested by the site, the sample will undergo microscopic analysis for red blood cells, white blood cells, and squamous epithelial cells.

At the Day 1 Visit, the subject will receive their first study drug application at the clinical site during the Baseline Visit. Subjects will be trained in the correct application of the study drug and provided an ample supply of study drug to complete BID (twice daily) dosing through Day 28. The first application of study drug will occur in the morning and the second application approximately 8 to 12 hours later. A diary will be maintained documenting compliance with application of the self-administered application and daily pruritus score. At the Day 29 Visit, the subject will be provided an ample supply of study drug to complete dosing through Day 56. At the Day 57 Visit, the subject will be provided an ample supply of study drug to complete dosing through Day 84. The final application of study drug will be applied by the subject on the evening of Day 84 or, if the Day 85 Visit is delayed, the evening prior to the Day 85 Visit.

Efficacy will be assessed through collection of the IGA, Signs of AD score, BSA of AD, EASI score, and changes in pruritus. An IGA will be conducted at Screening to ensure subject eligibility and again at Baseline (if not same day as Screening Visit) and Days 15, 29, 57 and 85. The IGA assesses the overall status of the AD lesions at the time of the assessment. Every effort should be made to have the IGA conducted by the same investigator/sub-investigator at each visit. No comparisons are made to previous assessments. The IGA is scored from 0 (Clear) to 4 (Severe) based on scoring system provided in Table 2.

The proportion of participants with an IGA target lesion score of clear (0) or almost clear (1) and a decrease of 2-grades or more will be presented.

TABLE 2

Validated Investigator Global Assessment scale for Atopic Dermatitis (vIGA-AD ™)[a]

The IGA score is selected using the descriptors below that best describe the overall appearance of the lesions at a given time point. It is not necessary that all characteristics under Morphological Description be present.

| Score | Morphological Description |
|---|---|
| 0 - Clear | No inflammatory signs of atopic dermatitis (no erythema, no induration/papulation, no lichenification, no oozing/crusting. Post-inflammatory hyperpigmentation and/or hypopigmentation may be present. |
| 1 - Almost | Barely perceptible erythema, barely perceptible induration/papulation, and/or clear minimal lichenification. No oozing or crusting, |
| 2 - Mild | Slight but definite erythema (pink), slight but definite induration/papulation, and/or slight but definite lichenification. No oozing or crusting, |
| 3 - Moderate | Clearly perceptible erythema (dull red), clearly perceptible induration/papulation, and/or clearly perceptible lichenification. Oozing and crusting may be present. |
| 4 - Severe | Marked erythema (deep or bright red), marked induration/papulation, and/or marked lichenification. Disease is widespread in extent. Oozing or crusting may be present. |

Notes:
In indeterminate cases, please use extent to differentiation between scores, for example: Patient with marked erythema (deep or bright red), marked papulation and/or marked lichenification that is limited in extent, will be considered "3 - Moderate".
Excoriations should not be considered when assessing disease severity.
[a]Copyright © 2017 Eli Lilly and Company - Used with the permission of Eli Lilly and Company under a Creative Commons Attribution - No Derivatives 4.0 International License - https://creativecommons.org/licenses/by-nd/4.0/

The Signs of AD score will be an examination of all lesions on the subject for the presence of erythema, exudation, excoriation, induration/papulation, and lichenification. Each sign will be graded according to the grade and definitions provided in Table.

TABLE 3

Signs of Atopic Dermatitis (Paller)

| Score | Grade | Definition |
|---|---|---|
| Erythema (redness) | | |
| 0 | None | No redness |
| 1 | Mild | Mildly detectable erythema; pink |
| 2 | Moderate | Dull red; clearly distinguishable |
| 3 | Severe | Deep, dark red; marked and extensive |
| Exudation (oozing and crusting) | | |
| 0 | None | No oozing or crusting |
| 1 | Mild | Minor or faint signs of oozing |
| 2 | Moderate | Definite oozing or crusting |
| 3 | Severe | Marked and extensive oozing or crusting |
| Excoriation (evidence of scratching) | | |
| 0 | None | No evidence of excoriation |
| 1 | Mild | Mild excoriation |
| 2 | Moderate | Definite excoriation |
| 3 | Severe | Marked, deep, or extensive excoriation |
| Induration/papulation | | |
| 0 | None | None |
| 1 | Mild | Slightly perceptible elevation |
| 2 | Moderate | Clearly perceptible elevation but not extensive |
| 3 | Severe | Marked and extensive elevation |

TABLE 3-continued

Signs of Atopic Dermatitis (Paller)

| Score | Grade | Definition |
|---|---|---|
| Lichenification (epidermal thickening) | | |
| 0 | None | No epidermal thickening |
| 1 | Mild | Minor epidermal thickening |
| 2 | Moderate | Moderate epidermal thickening; accentuated skin lines |
| 3 | Severe | Severe epidermal thickening; deeply accentuated skin lines |

The EASI score will be conducted by the principal investigator or an appropriately trained designee to obtain a score to measure the extent (area) and severity of AD. EASI will be scored using the area score for each of the four regions (head and neck, trunk, upper limbs, and lower limbs) of the body. The area score is the percentage of skin affected by atopic dermatitis (eczema) for each body region:

TABLE 4

Determination of EASI Score

| 1. Area score | Percentage of skin affected by eczema in each region |
|---|---|
| 0 | No active eczema in this region |
| 1 | 1-9% |
| 2 | 10-29% |
| 3 | 30-49% |
| 4 | 50-69% |
| 5 | 70-89% |
| 6 | 90-100%: the entire region is affected by eczema |

I-NRS

At each study visit, the subject will complete the Itch Numeric Rating Score (I-NRS).

The subject will be asked, "How would you rate your AVERAGE itch in the past 24 hours, on a scale from 0 to 10, where 0 is No itch and 10 is Worst itch imaginable?". Prior to morning application of the study drug, the subject will record in their diary the Worst Itch Numeric Rating Score (WI-NRS).

WI-NRS

Each day the subject will complete the Worst-Itch Numeric Rating Score (WI-NRS).

The diary question will read, "How would you rate your WORST itch in the past 24 hours, on a scale from 0 to 10, where 0 is No itch and 10 is Worst itch imaginable?"

For all subjects, assessment of compliance with study drug application will be conducted through collection of a study diary on which subjects will record their daily administration. In addition, subjects will be required to return all used and unused study drug at each visit where the study site will assess compliance. At each study visit the clinical site will weigh each pump dispensed to the subject and returned from the subject to calculate the amount of study drug used.

Statistical and Analytical Plans

The purpose of this Phase 2a study is to describe the safety and efficacy of treatment with the BTX 1204 4% Liquid Formulation vs Vehicle with BID dosing in subjects with moderate atopic dermatitis. Exploratory analysis of the study drug's effect on AD will be evaluated. None of these assessments will use hypothesis testing to assess their treatment effect.

This study will be evaluated using 3 analysis sets: intent-to-treat (ITT), per protocol (PP), and safety. Efficacy conclusions will be drawn from the ITT analysis set. The ITT analysis set will consist of all randomized subjects with at least one post-baseline efficacy assessment and will be based on randomized study group, regardless of study drug received. The PP analysis set will be used to support the efficacy findings in the ITT analyses and will include subjects with no major protocol deviations. Safety conclusions will be drawn from the safety analysis set. The safety analysis set will include all subjects that received at least one application of study drug and had at least one post-baseline safety assessment with treatment based on study drug received regardless of randomization group.

Demographics will be summarized using the safety analysis set by baseline age, gender, race, ethnicity, height, and weight. The primary efficacy analysis will be conducted on the ITT population. For continuous variables, the mean, standard deviation (SD), median, and range will be presented along with the 95% confidence interval (CI). Categorical variables will be summarized by proportions along with the 95% CI.

The efficacy variables include the IGA, BSA of AD, Signs of AD score, EASI score, and pruritus scores (I-NRS) collected at Screening/Baseline and all subsequent study visits and the WI-NRS recorded daily by subjects.

The primary efficacy endpoint for the study is the proportion of subjects with IGA success defined as an IGA score of Clear (0) or Almost Clear (1) with at least a 2-grade improvement from Baseline at Day 85. The IGA will be dichotomized into "success" and "failure" at study Day 15, Day 29, Day 57, and Day 85. Success on IGA defined as a score of Clear (0) or Almost Clear (1) and at least a 2-grade improvement from Baseline at Day 15, Day 29, Day 57, and Day 85 will be analyzed using logistic regression, adjusting for Baseline IGA.

Summary statistics will be prepared for the change from Baseline in the percent of BSA affected by AD at Days 15, 29, 57, and 85. The change from Baseline in BSA of AD will be analyzed used ANCOVA with Baseline BSA of AD and treatment as covariates.

Summary statistics will be presented for the change from baseline in each of the Signs of AD scores (erythema, exudation, excoriation, induration/papulation, and lichenification) at each timepoint (Day 15, Day 29, Day 57 and Day 85). A total score will be calculated based on the sum of each of the Signs of AD (0, 1, 2, or 3; max score of 15) and the change from baseline will be summarised for each timepoint. The change from baseline in Signs of AD score at Day 15, Day 29, Day 57, and Day 85 will be analyzed used ANCOVA with Baseline Signs of AD score and treatment as covariates.

The proportion of subjects with an EASI 50 and EASI 75 score will be summarized at Day 15, Day 29, Day 57, and Day 85 and compared using logistic regression, adjusting for Baseline EASI score. Summary statistics will be prepared for the change from Baseline in the EASI score and I NRS at each timepoint (Day 15, Day 29, Day 57 and Day 85).

Summary statistics will be prepared for the change from Baseline in the Signs of AD score for the target lesion (selected sites) at each timepoint (Day 15, Day 29, Day 57 and Day 85).

Summaries of the pruritus scores (WI-NRS) reported by the subjects in the daily Patient Diary will be presented using daily means by treatment and with graphic presentations.

The percent change from Baseline the EASI will be presented along with the subject's report of pruritus obtained from the Patient Diary. Time to improvement of pruritus and subject's assessment of the change in their AD from Baseline to Day 85 will be presented.

Outcomes

The efficacy of BTX 1204 4% (w/w) will be evaluated using the Validated Investigator Global Assessment scale for Atopic Dermatitis (vIGA-ADTM; heretofore—IGA), Body Surface Area (BSA) of AD, Signs of AD (erythema, exudation, excoriation, induration/papulation, and lichenification), and Eczema Area Severity Index (EASI) Scores completed by the treating dermatologist along with Itching-Numerical Rating Score (I-NRS) and Worst Itching NRS (WI-NRS) scores reported by subjects. At selected sites, a target lesion will be identified, photographed and scored with the Signs of AD.

The primary efficacy endpoint for the study will be the proportion of subjects with IGA success defined as an IGA score of "Clear" (0) or "Almost Clear" (1) with at least a 2-grade improvement from Baseline at Day 85.

The secondary endpoints for the study will be:

The proportion of subjects with an EASI 75 score at Day 85,

The proportion of subjects with an EASI 50 score at Day 85,

The change from Baseline in the Signs of AD score at Day 85,

The proportion of subjects with an IGA of Clear or Almost Clear at Day 85,

The proportion of subjects with at least a 2-grade improvement in ISGA from Baseline at Day 85, The change from Baseline in the percent of BSA affected by AD at Day 85, The time to achieve IGA success, and The change from Baseline to Day 85 in the I-NRS The exploratory endpoints will be:

The change from Baseline in the Signs of AD score at Day 15, Day 29, and Day 57, The change from Baseline in the percent of BSA affected by AD at Day 15, Day 29, and Day 57, The proportion of subjects with IGA success defined as an IGA score of "Clear" (0) or "Almost Clear" (1) with at least a 2-grade improvement from Baseline at Day 15, Day 29, and Day 57, The percent change from Baseline in the EASI Score at Day 85, Change from Baseline in the subject's reports of pruritus obtained daily on a Patient Diary.

Time to improvement of pruritus (change of 4 in the Worst Itch Numerical Rating Score [WI-NRS, 0-10 score]), Subject's assessment of the change in their AD from Baseline to Day 85 (Patient Reported Outcome [PRO]), and The change from Baseline to Day 29, and Day 57, and Day 85 in the Signs of AD score for the target lesion (at selected sites only).

Example 3

Residual cannabidiol concentrations for a range of compositions were measured before identifying the compositions most suitable for use in the dosage regimens of the present invention, as summarised in Table 5, below.

TABLE 5

Concentration of Cannabidiol (CBD) on skin after evaporation of volatile solvents

| Formulation | Initial CBD Concentration % w/w | Volatile Component(s) % w/w | Residual solvent(s) % w/w | Final CBD Concentration After Evaporation % w/w |
|---|---|---|---|---|
| 1 | 0.1 | 99.7 | 0.2 | 33.3 |
| 2 | 0.5 | 99.3 | 0.2 | 71.4 |
| 3 | 1.0 | 98.8 | 0.2 | 83.3 |
| 4 | 1.0 | 98.0 | 1.0 | 50.0 |
| 5 | 5.0 | 94.0 | 1.0 | 83.3 |
| 6 | 10.0 | 89.0 | 1.0 | 90.9 |
| 7 | 1.0 | 97.0 | 2.0 | 33.3 |
| 8 | 5.0 | 93.0 | 2.0 | 71.4 |
| 9 | 10.0 | 88.0 | 2.0 | 83.3 |
| 10 | 1.0 | 96.0 | 3.0 | 25.0 |
| 11 | 5.0 | 92.0 | 3.0 | 60.0 |
| 12 | 10.0 | 87.0 | 3.0 | 76.9 |

TABLE 6

Compositions for use in one or more of the abovementioned studies

| Ingredient | BTX 1204 Prototype 4% CBD$^c$ | BTX 1204 for Phase II Clinical Study BTX 2018.003 4% CBD$^{a,b}$ | Function |
|---|---|---|---|
| Cannabidiol(CBD) | 4.0 | 4.0 | Active ingredient |
| Hexamethyldisiloxane (HDS) [Dow Q7 -9180 Silicone Fluid 0.65 CST] | 94.5 | 87.0 | Volatile solvent |
| Polypropylene Glycol-15 (PPG-15) Stearyl Ether [Arlamol PS15E] | 1.5 | 1.0 | Emollient |
| Dow Corning ® 1515 Gum | — | 5.0 | Viscosity modifier |
| Isopropyl Alcohol (IPA) | — | 3.0 | Solvent |
| Total | 100 | 100 | Not applicable |

Study BTX.2018.003 is presented above as Example 2.

Numerous variations and modifications of the above-described modes of carrying out the various embodiments of this invention will be apparent to those skilled in the art, based on the above teachings related to the disclosed invention, without departing from the basic inventive concepts. The above embodiments of the invention are merely exemplary and should not be construed to be in any way limiting and all such variations and modifications are to be considered within the scope of the present invention, the nature of which is to be determined from the foregoing description.

The invention claimed is:

1. A treatment regime for use in the treatment of dermatitis and inflammatory skin conditions, said regime comprising the administration of:
   between 50 mg and 3000 mg of a topical liquid or gel composition comprising between 1% w/w and 15% w/w cannabidiol, 85% w/w and 95% w/w of hexamethyldisiloxane, octamethyltrisiloxane or combinations thereof, and between 1% w/w and 10% w/w of a residual solvent that is less volatile than hexamethyldisiloxane, octamethyltrisiloxane or combinations thereof such that less than 5% of the residual solvent evaporates at skin temperature over 24 hours and wherein the residual solvent is selected from fatty acids, fatty acid alcohols, fatty alcohols, glycols or alkanes, or ethers of any of these, wherein the cannabidiol is dissolved in the liquid or gel composition, and the total daily dose applied to the skin is between 20 mg and 2000 mg cannabidiol.

2. The treatment regime of claim 1, wherein the topical composition is administered to the skin between 1 and 5 times per day.

3. The treatment regime of claim 1, wherein the topical composition delivers between 20 mg and 400 mg of cannabidiol per administration.

4. The treatment regime of claim 1 wherein:
   the topical composition comprises 4% w/w cannabidiol.

5. The treatment regime of claim 1, wherein the topical composition comprises 1-10% wt/wt C2-C6 alcohol.

6. The treatment regime of claim 1, wherein the topical composition comprises 85% w/w and 95% w/w hexamethyldisiloxane.

7. The treatment regime of claim 1, wherein the residual solvent is a compound selected from the group consisting of: alkyl polypropylene glycol, polyethylene glycol ether, oleyl alcohol, isostearyl alcohol, octyldodecyl alcohol, 2-hexyl decyl alcohol, isohexadecane.

8. The treatment regime of claim 1 wherein the regime delivers 180 mg of cannabidiol per day.

9. The treatment regime of any of claims 1-3, 4, 5, 6, 7 and 8 for use in the treatment of dermatitis.

10. The treatment regime of any of claims 1-3, 4, 5, 6, 7 and 8 for use in the treatment of atopic dermatitis.

* * * * *